United States Patent [19]

Hill et al.

[11] 4,153,668

[45] May 8, 1979

[54] MULTI-ZONE ANALYTICAL ELEMENT AND METHOD USING SAME

[75] Inventors: Doyle E. Hill, Fairport; Karl J. Sanford, Rochester, both of N.Y.

[73] Assignee: Eastman Kodak Company, Rochester, N.Y.

[21] Appl. No.: 866,732

[22] Filed: Jan. 3, 1978

[51] Int. Cl.$^2$ ............................................. G01N 33/16
[52] U.S. Cl. ........................................ 422/56; 23/902; 195/103.5 R; 422/57
[58] Field of Search .......................... 23/253 TP, 902; 195/103.5 R

[56] References Cited

U.S. PATENT DOCUMENTS

| | | | |
|---|---|---|---|
| 3,867,258 | 2/1975 | Forgione | 195/103.5 R |
| 3,901,657 | 8/1975 | Lightfoot | 23/253 TP |
| 3,992,158 | 11/1976 | Przybylowicz et al. | 23/253 TP |
| 4,050,898 | 9/1977 | Goffe et al. | 23/253 TP |
| 4,069,017 | 1/1978 | Wu et al. | 23/253 TP X |

*Primary Examiner*—R. E. Serwin
*Attorney, Agent, or Firm*—Ronald P. Hilst

[57] ABSTRACT

A multi-zone analytical element for the analysis of a proteinaceous or protein-bound substance contained in an aqueous liquid and a method of using the same are disclosed. The multi-zone element contains a spreading zone and a reagent zone in fluid contact. The reagent zone of the element contains an interactive composition. Incorporated in the spreading zone of the element is an immobilized polymeric material containing charge-bearing functional groups that, under conditions of use of the element, exhibit an electric charge opposite to that of said proteinaceous substance or the protein portion of said protein-bound substance.

15 Claims, No Drawings

MULTI-ZONE ANALYTICAL ELEMENT AND METHOD USING SAME

FIELD OF THE INVENTION

The present invention relates to an element useful for the chemical analysis of liquids. More particularly, it concerns multi-zone elements that provide an improved means for determining the presence and/or concentration of a proteinaceous or protein-bound substance contained in an aqueous liquid.

DESCRIPTION OF RELATED ART

It is often desirable or necessary to determine the presence and/or concentration of certain substances in aqueous liquids, particularly biological liquids such as blood, serum, and urine. A variety of devices and methods have been employed for such analyses. Because of convenience, low cost, and the rapidity by which analyses can be carried out, it has often been found desirable to carry out analyses of such aqueous liquids by use of various so-called "dry-chemistry" techniques. The term "dry chemistry" refers herein to analytical chemical techniques wherein chemical reagents, sometimes referred to hereinafter as interactive compositions, are incorporated in various substantially "dry-to-the-touch" elements. Typical "dry-to-the-touch" elements include "dip-and-read" test strips, e.g., monolayer test strips, and multi-zone analytical test elements, e.g., multilayer elements.

Prior to the present invention, depending upon the particular substance under analysis, sometimes referred to hereinafter as analyte, or upon the particular reagents contained in the test element, various additional materials have been incorporated into one or more zones of "dry chemistry" test elements to facilitate a particular analysis or to solve a specific problem which has been found to arise in a particular analysis.

For example, in U.S. Pat. No. 3,901,657 issued Aug. 26, 1975 there is disclosed a multilayer element for the determination of various analytes, particularly drugs such as alkaloids, amphetamines, synthetic analgesics, catecholamines and other nitrogenous bases, contained in aqueous fluids. The multilayer test element of this patent is asserted to be especially suitable for the determination of morphine in urine. According to this patent, a polymeric or non-polymeric material containing functional groups which are capable of reacting with, absorbing, or otherwise combining or attracting morphine in the urine sample is incorporated into the surface layer of the multilayer element so as to concentrate any morphine contained in the particular sample being tested. By so concentrating the morphine, the subsequent interaction of the morphine with other reagents present in this multilayer test element is enhanced. Among the various polymeric or non-polymeric materials containing functional groups which are suggested in U.S. Pat. No. 3,901,657 for use in concentrating analytes such as cations and basic organic compounds such as morphine are acidic polymeric materials, e.g., cationic exchange resin materials. In the case where the analyte under investigation by the multilayer element test element disclosed in U.S. Pat. No. 3,901,657 tends to become anionic, it is suggested that the polymeric or non-polymeric material used to concentrate the analyte be selected from materials which contain positively charged functional groups, e.g., anionic exchange resins.

In contrast to the multilayer elements of U.S. Pat. No. 3,901,657 which are primarily concerned with the analyses of aqueous liquids for various drugs contained therein, U.S. Pat. No. 3,867,258 issued Feb. 18, 1975 is directed to a monolayer diagnostic test element for the determination of the enzyme lactate dehydrogenase in aqueous liquids such as serum. The test element of U.S. Pat. No. 3,867,258 generally is composed of a porous multilayer material, such as a cellulosic paper, which is impregnated with the immobilized enzyme diaphorase and the dried residue of a color-forming reagent material composed, at least in part, of a dye-forming tetrazolium salt. U.S. Pat. No. 3,867,258 discloses that additional materials may also be incorporated in the monolayer test elements described therein including polyanionic materials such as poly(methacrylic acid), polyacrylic acid, carboxymethyl cellulose and copolymaleic acid-methylvinylether. These polyanionic materials are incorporated to prevent the chromatographic movement of the colored dye form of the tetrazolium salt which is produced in these elements in the presence of lactate dehydrogenase.

More recently, U.S. Pat. No. 3,992,158 issued Nov. 16, 1976 and U.S. Pat. No. 4,050,898 issued Sept. 27, 1977, disclosed certain improved multi-zone analytical elements for the analysis of liquids. In the element disclosed in U.S. Pat. No. 3,992,158 there is present a reagent layer as a reagent zone and a spreading layer as a spreading zone, the latter layer being isotropically porous and preferably containing a non-fibrous material. When the spreading layer of the element is spotted with a sample of aqueous liquid to be tested for a particular analyte, this layer has been found to be especially effective in receiving the liquid test sample and distributing such liquid within itself in a manner to provide a substantially uniform concentration of any analyte for interaction with the reagent components of the element. The reagent layer of the analytical elements of the U.S. Pat. No. 3,992,158 patent contains any of various compositions interactive with the desired analyte to provide, for example, a radiometrically detectable species indicative of the presence and/or concentration of the analyte. The analytical elements disclosed in the U.S. Pat. No. 3,992,158 patent may be used in the analysis of a variety of blood components including glucose, uric acid, proteinaceous materials such as albumin, and many others.

The above-referenced U.S. Pat. No. 4,050,898 discloses that by incorporating a relatively large amount of a surfactant material, such as an ionic or nonionic surfactant, into the spreading layer of an analytical element of the type described in U.S. Pat. No. 3,992,158, there is provided an element particularly useful for the assay of analytes dissolved in proteinaceous aqueous liquids. As described in U.S. Pat. No. 4,050,898, the incorporation of a nonionic surfactant, such as octyl phenoxy polyethoxy ethanol, into the spreading layer is effective to normalize transport within the spreading layer of an analyte dissolved in various applied samples of proteinaceous liquid, notwithstanding variations in protein concentration which may exist among the various liquid samples. The manner by which such normalization occurs as disclosed in the aforementioned patent is not fully understood. However, the patent indicates that the amount of surfactant used appears to decrease the water of hydration of proteins contained in the applied liquid sample. For this reason it is theorized that a greater amount of the water contained in the sample, as well as a greater amount of the dissolved analyte, is able to rapidly penetrate into the spreading layer and reagent layer of the multilayer element. Thus, the rate of indicating reactions which occur in the element is facilitated, regardless of varying amounts of proteinaceous material which may be present among individual aqueous samples presented for analysis.

The multi-zone elements disclosed in U.S. Pat. Nos. 3,992,158 and 4,050,898 have been found especially useful for analysis of aqueous liquids. In part, this is because the spreading layer of these elements has been found to be particularly effective in avoiding the problem of chromatographic effects which can arise due to the non-uniform lateral migration of analytes within these test elements. This problem occurs because of the tendency of the analyte contained in an applied aqueous sample to become non-uniformly distributed within the test element, i.e., to undergo chromatographic effects within the element, thereby leading to non-uniform interaction of analyte and the reagent materials incorporated in the element. Therefore, detectable species which are formed in the multi-zone element as a result of the reaction between the analyte and the interactive composition tend to be formed in a manner which does not accurately or precisely reflect actual quantitation of the analyte contained in the liquid sample. This problem is sometimes referred to in the art as "chromatographing," "ringing," "targeting," or "doughnuting."

As further indicated, analytical elements of the type described in U.S. Pat. Nos. 3,992,158 and 4,050,898 are particularly useful for the detection of analytes in proteinaceous aqueous liquids. However, it has been found that due to the high molecular weight and large size of many protein molecules, e.g., albumin and globulins, as well as complexes of protein with substances which bind to protein, such as lipids, e.g., serum cholesterol and triglycerides, "chromatographing" becomes more difficult with respect to these particular analytes and in some cases is apparent even in multilayer elements of the type described in U.S. Pat. Nos. 3,992,158 and 4,050,898.

The four patents discussed hereinabove disclose a variety of "dry chemistry" analytical elements. However, these patents appear to have no disclosure as to specific materials that can be incorporated into a multi-zone analytical element especially adapted for the assay of a proteinaceous or protein-bound analyte and which can further reduce or eliminate the above-described problem of chromatographing with respect to these particular analytes.

SUMMARY OF THE INVENTION

In accord with the present invention there is provided an analytical element and method for the analysis of a proteinaceous or protein-bound analyte contained in an aqueous liquid. The analytical element of the invention is a multi-zone element, for example, an integral multilayer analytical element, and typically comprises a spreading zone to receive and distribute within itself a sample of the aqueous liquid to be analyzed, and a reagent zone in fluid contact with the spreading zone under conditions of use of the element. The reagent zone contains an interactive composition for the desired proteinaceous or protein-bound analyte, or a reaction or decomposition product thereof, so that a detectable change is produced within the element indicative of the presence and/or concentration of the analyte in the aqueous liquid sample.

In accord with the improvement of the present invention there is incorporated within the spreading zone of the above-described multi-zone element an immobile polymeric material which (a) is non-interfering with respect to the aforesaid interactive composition and (b) contains charge-bearing functional groups that, under conditions of use of the element, exhibit an electric charge opposite to that of the proteinaceous analyte or the protein portion of a protein-bound analyte. As a result, the above-described chromatographing problem exhibited by a proteinaceous or protein-bound analyte within the spreading zone of a multi-zone analytical element is substantially reduced or eliminated.

The improved multi-zone analytical elements of the present invention are particularly useful in analyses of various biological liquids such as serum and urine for proteinaceous analytes, especially albumin, globulin, and total protein. The analytical elements are also useful in analyses of analytes such as lipids, for example, cholesterol and triglycerides, which complex with proteinaceous materials contained in biological liquids. Analytes which complex with or otherwise bind to proteinaceous materials are referred to herein as "protein-bound" analytes.

In accord with a further aspect of the invention, there is provided an improved method for the analysis of a proteinaceous or protein-bound analyte in an aqueous liquid sample which comprises using the above-described multi-zone element. This can be achieved by contacting the spreading zone of the above-described multi-zone element with the aqueous liquid sample and detecting, after a predetermined time, the detectable change produced in this element in response to the presence and/or concentration of the desired proteinaceous or protein-bound analyte.

DESCRIPTION OF PREFERRED EMBODIMENTS

The above-described polymeric materials incorporated into the spreading zone of a multi-zone element of the present invention are believed to substantially reduce or eliminate the chromatographing of proteinaceous or protein-bound analytes contained in test samples of aqueous liquids spotted thereon for several reasons. Among others, it is believed that the charge-bearing functional groups of these polymer materials tend to attract, through electrical interaction, proteinaceous analytes contained in the aqueous liquid under analysis. Proteinaceous materials tend to exhibit either a net positive or a net negative electric charge in aqueous liquids depending upon the pH of the liquid. Under alkaline conditions, i.e., at pH levels of 8 and higher, proteinaceous materials tend to exhibit a negative charge. Accordingly, in such case one would select as a suitable polymeric material a polymer which has appended thereto functional groups which exhibit or acquire a positive charge under alkaline conditions. On the other hand, under acidic conditions, i.e., at pH levels less than about 5, proteinaceous materials contained in aqueous liquids tend to exhibit a positive charge. Accordingly, in this case one would incorporate into the spreading zone of an improved multi-zone element of the present invention a polymeric material having functional groups exhibiting a negative charge character under acidic conditions. At intermediate pH levels between about 5 and 8, the net electrical charge exhibited by proteinaceous materials, if any, will depend upon the particular material and the aqueous environment in which the material is incorporated. By virtue of the electrical interaction between the proteinaceous analytes and the polymeric material incorporated into the spreading zone of an element of the invention, the natural tendency of the proteinaceous analyte to exhibit chromatographing in the spreading zone is effectively prevented or, at least, substantially reduced. The electrical interaction tends to maintain a uniform distribution of the proteinaceous material of the applied aqueous test sample within the spreading zone to which the liquid test sample is applied.

In addition, by virtue of the polymeric character of the polymeric material used in accord with the present invention, the mobility of this material within the spreading zone in the presence of an applied aqueous test sample is, itself, substantially prevented. In this regard, it will be appreciated that the mere presence of a charge-bearing functional group within the spreading zone of a multi-zone analytical element is insufficient to provide the advantageous results obtained in accord with the present invention. That is, if the charge-bearing functional species is itself capable of migration within the spreading zone, for example, due to solvent interaction with other compositions in the spreading zone matrix or due to migration in the presence of the applied aqueous liquid test sample, the desirable advantages which might otherwise be provided by such charge-bearing functional species can be effectively destroyed.

To overcome the above-described migration problem which can be exhibited by otherwise electrically effective charge-bearing species, it has been found that the addenda incorporated into the spreading zone should be a polymeric material having sufficient molecular weight to effectively immobilize it within the spreading zone under conditions of use of the element and under ordinary storage and keeping conditions of the element. In general it has been found preferable to select as useful polymeric materials, polymers having a molecular weight of at least 10,000, as measured by, for example, gel chromatography.

It will be appreciated that, depending upon the conditions under which a particular assay is carried out, for example, temperature and pH conditions, the polymeric material useful in the present invention may be quite varied. For example, a polymeric material which exhibits little or no migration within the spreading zone of a multi-zone element under normal room temperature and keeping conditions may exhibit undesirable migration effects at an elevated temperature level at which the particular assay to be carried out by this multi-zone element is to be performed. However, this same polymeric material may be perfectly suitable for use in other multi-zone elements within the scope of the present invention if the particular assays to be carried out by such elements are run at lower temperatures. Likewise, one should consider the pH level of the spreading zone which is established during the assay carried out by a particular multi-zone element because the mobility of certain polymeric materials may be pH dependent.

As indicated above, polymeric materials suitable for use in accord with the present invention have attached thereto charge-bearing functional groups, such groups exhibiting either a positive or a negative charge, depending upon the charge properties assumed by the proteinaceous analyte under the particular assay conditions to be employed. As will be appreciated, the essential requirement is that the particular functional group selected should exhibit an electrical charge opposite to that of the proteinaceous analyte under the particular conditions of use and be chemically non-interfering as to the interactive composition of the element. For example, in one embodiment of the present invention there is provided a multi-zone element for the determination of the total protein content of a serum sample. In this embodiment, the interactive composition to be employed in the reagent zone of the element is advantageously a biuret reagent composition which under high pH conditions, i.e., pH levels in excess of 12, undergoes interaction with proteinaceous materials contained in the serum sample to yield a colored species which is readily detectable within the element. In this embodiment, the polymeric material selected for use within the spreading zone of the element should be a polymeric material to which are attached functional groups exhibiting a positive charge under high pH conditions. As a result these polymeric materials are capable of attracting the proteinaceous materials within the serum sample because these proteinaceous materials tend to exhibit a negative-charge under high pH conditions.

As indicated above, the choice of a particular charge-bearing functional group to be attached to the polymeric material employed in the spreading zone of the multi-zone elements of the present invention is, in large part, dictated by whether one desires a negative charge- or positive charge-bearing group. A partial listing of representative functional groups which are useful in the polymeric materials of the present invention and which exhibit a negative charge includes carboxy groups, sulfonic groups, phosphonic groups, sulfonate groups, and equivalent such groups. In general, any anionic polymer is useful as a polymer containing negative charge-bearing functional groups.

Typically, polymeric materials containing weak acidic groups such as carboxy groups, or other similar members in the aforementioned list of negative charge-bearing functional groups, exhibit such negative charge character at pH levels of about 3.5 or higher. Thus, in order for such functional groups to be useful as negative charge-bearing groups, the polymeric material containing such groups must be incorporated into the spreading zone of a multi-zone element that is to be used in an assay which employs pH levels of 3.5 or more. For example, carboxymethyl cellulose represents a particularly useful polymeric material which may be employed in the spreading zone of a multi-zone element of the invention. The carboxy groups appended to this polymeric material exhibit a negative charge when the polymer is maintained in an environment having a pH in excess of about 3.5. If levels less than about 3.5 are encountered, this polymeric material becomes essentially a neutral species. On the other hand, strong acid groups, such as sulfonate groups, exhibit a negative charge character at pH levels as low as 1 or 2 (and, of course, at pH levels higher than 1 or 2 as well).

As will be appreciated, there are a variety of functional groups exhibiting a positive charge value which may be attached to polymeric material useful in the present invention. Typical examples of positive charge-bearing functional groups are various amino groups such as aliphatic amino groups, alicyclic amino groups, and aromatic amino groups, including aromatic amines having a nitrogen atom attached to a benzene nucleus or other carbocyclic aromatic nucleus and aromatic amines having a nitrogen atom present as a ring member in an unsaturated aromatic heterocyclic nucleus, for example, a pyridine or pyrrole nucleus. In general, these amino functional groups exhibit a positive charge value under pH conditions of about 9.0 or lower. A representative example of one such material is diethylaminoethyl cellulose.

In addition to the foregoing materials, another useful class of positive charge-bearing functional groups which may be employed are cationic polymers bearing groups which exhibit a positive charge regardless of the pH conditions in which they are used, e.g., ammonium groups, phosphonium groups, and equivalents thereof. For example, a cationic polymer such as poly(vinyl benzyltrimethyl ammonium chloride) represents a useful polymeric material containing a cationic functional group.

The polymeric backbone of the polymeric material to which the above-described charge-bearing functional groups are attached may be selected from a wide variety of materials and is not particularly critical to the present invention. For example, polymeric backbones comprising addition polymers such as vinyl polymers; condensation polymers such as polyesters; cellulosic polymers; etc. may be employed. As will be appreciated, the particular manner of making polymeric materials for use in the invention is also a non-critical feature of the invention, and a variety of conventional polymerization techniques such as suspension polymerization, emulsion polymerization and solution polymerization may be employed.

The amount of polymeric material useful in the spreading zone of the present invention will, to a large extent, vary depending upon the number of charge-bearing functional groups attached to a specific polymeric material, the particular assay conditions, the particular analyte, and the analyte concentration range over which a specific multi-zone element of the present invention is intended for use. In general, useful amounts of a particular polymeric material can be selected by incorporating a series of increasing concentration levels of the particular polymeric material under consideration into the matrix of the desired spreading zone and observing the effect these varying concentration levels have on reducing the chromatographing problem of the proteinaceous or protein associated analyte discussed hereinabove. In such case, one typically would employ an amount of polymeric material producing optimum reduction of protein chromatographing without deleteriously affecting other desirable properties of the spreading zone. In preferred embodiments, such desirable properties include adhesion to other zones or layers of the multi-zone element, its preparation such as by conventional coating or paper making techniques, and the like. In general, it has been found that an amount of polymeric material within the range of from about 0.1 to about 40 weight percent based on the dry weight of all components contained in the spreading zone provides useful results. However, as illustrated in Example 4 hereinafter, amounts of such materials outside this range can also be useful in accord with the invention. Typical examples of useful amounts of polymeric material which have been found effective in accord with preferred embodiments of the present invention are illustrated hereinafter in the working examples appended to the present application.

As indicated hereinabove, the polymeric material employed in the present invention is incorporated into a spreading zone of a multi-zone element typically comprising at least two distinct zones, namely the spreading zone and a reagent zone, which are in fluid contact with one another under conditions of use of the multi-zone element. As explained hereinabove, the spreading zone function is to receive and distribute therewithin, an applied sample of the aqueous liquid to be analyzed for the desired proteinaceous analyte or protein-bound analyte. Upon application of the aqueous liquid sample to the spreading zone, the liquid sample is readily distributed within the spreading zone due to its spreading properties; and fluid components of the sample are thereby metered into contact with the reagent zone of the element.

The spreading zone and reagent zone can be present in typical multi-zone elements of the invention as superposed, contiguous layers or they may be present in such elements as superposed layers separated by various intervening subbing layers, registration layers, filtering layers, radiation-blocking layers and the like as further described hereinafter. Alternatively, rather than being superimposed one over the other, the various zones present in the elements of the invention may be present as adjacent, abutting zones of a multi-zone element. Preferably, in accord with certain embodiments of the present invention, the multi-zone elements contain a spreading zone which is superposed over a reagent zone, both of such zones being suitably defined by layers carried on a suitable support. For purposes of convenience and for illustrating the best mode of the invention, the multi-zone elements of the invention will be described hereinafter in terms of their presently preferred structure and characteristics as observed in an integral multilayer analytical element. In such preferred embodiments, a spreading layer is the spreading zone. However, it will be appreciated, as indicated hereinabove, that a variety of other configurations and structures may embody the invention broadly described herein.

A spreading zone or layer as used in the multi-zone element of the invention may be prepared from a wide variety of materials which serve the above-described spreading function. Typically such materials include various fibrous as well as non-fibrous compositions which are porous or permeable to the particular aqueous liquid sample being analyzed. Accordingly, such layers or zones may be prepared from typical filter paper materials, various semi-permeable synthetic polymeric membranes, and the like.

In accord with one preferred embodiment of the invention, the spreading zone represents a substantially non-fibrous, isotropically porous layer. Such layers can be prepared using various materials such as blushed polymer layers, optionally containing various particulate materials such as glass beads; plastic beads; pigments, e.g., titanium dioxide; particles of diatomaceous earth; microcrystalline colloidal materials, e.g., "microcrystalline cellulose;" and the like distributed therewithin. Extensive description, including methods for the preparation, of such non-fibrous, isotropically porous spreading layers may be found by reference to U.S. Pat. No. 3,992,158 referred to earlier herein. Spreading layers may be either opaque or transparent depending upon the specific materials which comprise a particular spreading layer and the pore size of the layer.

The polymeric materials used in the present invention may be incorporated into a spreading zone or layer by impregnating the layer or zone with a solution or dispersion of the polymeric material described herein. Alternatively, the polymeric materials described for use herein may be incorporated in these compositions by incorporating the polymeric material into the coating dope or formulation from which the spreading layer or zone is prepared or cast.

Reagent zones or layers in the elements of the invention are typically radiation-transmissive, that is, they will transmit electromagnetic radiation in the range of the spectrum used to determine the presence and/or concentration of the detectable species which is formed in the multi-zone element as a result of interaction with the desired proteinaceous or protein-bound analyte. Typically, the reagent zone or layer is also permeable or porous to the liquid components of the aqueous sample under test and may also be porous or permeable to certain analyte components contained in the liquid sample.

Within the reagent zone or layer is distributed a composition that can interact with the proteinaceous analyte or protein-bound analyte, or a reaction or decomposition product of such analyte which the particular element is designed to detect. Such interaction typically causes the release of a preformed detectable species contained in the reagent layer or the formation of a detectable species. The detectable species may be formed in the reagent zone or in the spreading zone to which precursors of the detectable species can migrate by virtue of the aqueous liquid which permeates into the reagent zone.

"Interaction" between a suitable composition and the particular proteinaceous analyte or protein-bound analyte is used herein to refer to chemical activity, catalytic activity as in the formation of enzyme-substrate complex, or any other form of chemical or physical interaction that can release, produce, or otherwise provide within the multi-zone element of the invention a species that is detectable and indicative of the presence and/or concentration of a desired proteinaceous or protein-bound analyte. Preferably, the detectable species that is produced is a radiometrically detectable species, i.e., a species that is detectable by use of electromagnetic radiation measuring techniques, sometimes referred to as radiometric techniques. Typical radiometrically detectable species include materials such as dyes which are detectable by fluorometric or colorimetric techniques.

The matrix of the reagent zone or layers used in the present invention in combination with the aforementioned interactive materials may be selected from a variety of materials including various fibrous materials such as filter paper materials and the like; various natural polymeric materials such as hydrophilic colloids including gelatin, agarose, polysaccharides, and the like; and various synthetic polymeric materials such as poly(vinyl alcohol), poly(vinyl pyrrolidone), poly(acrylamides) and the like.

The particular interactive composition incorporated into a reagent zone for use in the multi-zone elements of the present invention can be widely varied. Clearly, the choice of a particular interactive composition depends upon the specific proteinaceous analyte or protein-bound analyte which the element is intended to detect. For example, as indicated hereinabove, one useful interactive composition which may be employed when the element is intended for use as a total protein assay is a biuret reagent composition. Biuret compositions, as is well-known, typically include a cupric salt reagent and optionally a chelating agent therefor. Under highly alkaline conditions, the cupric salt undergoes a reaction with protein to produce a blue-violet color. One particularly useful biuret reagent composition is that described in Eikenberry and Sanford, U.S. patent application Ser. No. 866,731, filed concurrently herewith. These compositions are substantially free from sodium ion and include a water soluble cupric salt and a copper salt chelating agent precursor, such as tartaric acid. Other typical interactive compositions for proteinaceous analytes include various dyes such as various pH indicating dyes which, in the presence of protein molecules, undergo a dye-binding effect to produce a characteristic color change. A variety of such materials are available and known for use in this connection including such dyes as Congo red, Phenol red (phenolsulfonephthalein, tetrabromophenolphthalein, etc.).

In addition to total protein assays the multi-zone elements of the invention are also useful for assay of other proteinaceous analytes such as albumin, and various protein-bound analytes such as lipids, including cholesterol and triglycerides. The multi-zone elements of the invention are especially useful for the analysis of high molecular proteins, for example, proteins having a molecular weight in excess of 60,000 dalton units, because of the above-described chromatographing problem exhibited by these materials. In addition, various other proteinaceous analytes such as high molecular weight enzymes and the like which tend to exhibit a similar chromatographing problem may also be assayed using a multi-zone analytical element embodying the invention described herein to produce more precise and accurate results. As will be apparent, the particular interactive composition selected for such other proteinaceous and protein-bound analytes includes interactive compositions other than those described hereinabove in connection with a total protein assay. For example, in the assay of albumin, one may employ interactive compositions comprising a bromocresol green dye which, by virtue of its binding affinity to albumin, has been found to provide a useful method for quantitating albumin contained in various aqueous liquids. See Doumas, et al., *Clin. Chem. Acta.*, Vol. 31, page 87, (1971). In the case of lipid analytes such as cholesterol and triglycerides, interactive compositions for these materials may be selected from various materials and reagents described in the literature. For example, Davidsohn and Henry, in *Clinical Diagnosis*, 15th Ed., pages 635–639, provide a general review of various materials and reagents which have been found useful in conducting cholesterol and triglyceride assays.

In addition, if necessary or desirable, appropriate buffer compositions may also be present in either or both of the reagent and spreading zone of the multi-zone elements of the present invention. Various buffering compositions can be effectively employed in the multi-zone elements of the present invention including phosphate buffers as well as any of a wide variety of other buffer compositions such as those described by G. Good in *Biochemistry*, Vol. 5, page 467 (1966).

Certain of the above-described interactive compositions for use in the assay of proteinaceous or protein-bound analytes take place at high pH levels, for example, the above-noted biuret reagent composition for total protein requires a pH of about 12.0 or higher. In these circumstances it may be desirable to incorporate a high pH-providing composition in the analytical elements of the invention to provide the necessary pH level to carry out the desired assay. One particularly useful type of high pH-providing composition is that described in the aforementioned Eikenberry and Sanford, U.S. patent application Ser. No. 866,731, filed concurrently herewith. These high pH-providing compositions contain a mixture of a base of sufficient strength to provide a pH in excess of 12.0 and an alkaline-protective polymer, e.g., a copolymer of acrylamide and vinyl pyrrolidone.

In the case where the various materials contained in the spreading zone and/or reagent zone of the analytical elements of the invention represent self-supporting materials the analytical elements can be prepared without the aid of a separate supporting layer or material. However, in certain preferred embodiments of the invention wherein the spreading zone is present in the element as a layer superposed over a reagent layer, it is often found desirable to support the respective layers of the element on a separate radiation-transmissive support. Such a support transmits electromagnetic radiation in the range of the spectrum used to determine the presence and/or concentration of the detectable species. Various useful support layers include film-forming polymers such as cellulose acetate, polyethylene terephthalate, and the like. Further description of such useful radiation-transmissive supports which can be employed in the present invention are described in U.S. Pat. No. 3,992,158.

U.S. Pat. No. 3,992,158 discloses extensive information regarding effective pore sizes, dry thicknesses, and the like of spreading and reagent layers which can also be used in the spreading and reagent layers or zones employed in the elements of the present invention. Typically, a spreading layer having a dry thickness of from about 50 to about 300 microns and a pore size within the range of about 1 to about 30 microns, is useful in the present invention. As will be appreciated, these parameters may vary fairly widely depending upon the molecular weight and size of the particular proteinaceous or protein-bound analyte under consideration as well as the molecular weight of other components which may be present in a particular aqueous sample to be assayed. In addition, these parameters may vary significantly depending upon the composition of a spreading zone. For example, preferred non-fibrous, isotropically porous spreading layers of the type described hereinabove typically have a dry thickness and pore size within the above-referred to ranges. However, spreading zones prepared from fibrous materials such as various filter papers and the like may differ. Representative dry thicknesses for a useful reagent layer typically are within the range of from about 10 to about 100 microns, when such layers are prepared from a matrix composed of synthetic or naturally-occurring, film-forming coated materials. However, in the case where the matrix of a reagent layer is composed of various fibrous filter paper materials, layers having thicknesses outside this range may also be employed.

As noted hereinabove, multilayer analytical elements of the invention can also contain various additional zones or layers including subbing zones to aid in adhering adjacent zones of an element; registration zones to receive reaction products or detectable species released or formed in an element of the invention; filtering zones to filter out or remove particular components of applied liquid samples; radiation-blocking and reflecting zones to block and/or reflect certain wavelengths of radiation which are used to detect the presence and/or amount of a detectable species located in a particular zone of an element of the invention; and the like. Methods of preparing and incorporating these zones in analytical elements of the invention are identical or similar to such methods as described in U.S. Pat. No. 3,992,158 noted above and Clement, U.S. Pat. No. 4,042,335, issued Aug. 16, 1977, both of which are incorporated herein by reference. Accordingly, extensive description of such zones is unnecessary herein. Likewise, description of various analytical procedures, including manual and automated procedures, which can employ multi-zone analytical elements of the present invention are described and may be referred to in the aforementioned patents.

The following examples are presented to further illustrate the present invention.

EXAMPLE 1

Incorporation of Positive Charge-Bearing Polymers into the Spreading Layers of Analytical Elements for the Determination of Total Protein A series of three different multilayer analytical elements for the assay of total protein in serum was prepared. The elements employed a biuret reagent composition for the determination of total protein. See *Clinical Chemistry, Principles and Technics,* 2nd Ed., R. J. Henry et. al., p. 405, Harper & Row, N.Y., N.Y. (1974) and the aforementioned Eikenberry and Sanford application for a detailed discussion of the biuret reagent method for the determination of total protein. Each of the elements was prepared in an identical manner, except that the reflecting spreading layer of the elements was varied. One element, a control element, was prepared having a conventional non-fibrous, isotropically porous spreading layer formulation of the type described in U.S. Pat. No. 3,992,158 containing particulate microcrystalline cellulose incorporated in a poly(vinylpyrrolidone) binder. See spreading layer formulation 2 of Table I below. The remaining two elements contained spreading layer formulations modified by inclusion of certain polymeric materials. One of these elements had spreading layer formulation 3 of Table I containing a diethylaminoethyl cellulose polymer. The other of these elements employed spreading layer formulation 5 of Table I containing the cationic polymer poly(vinylbenzyltrimethylammonium chloride) purchased from Dow Chemical Co. under the tradename ECR-34. Each of the three elements of this Example was prepared as follows:

Each of three transparent polyethylene terephthalate film supports was coated with identical biuret reagent layers having a dry coating composition consisting of agarose (2.7 g/m$^2$) as binder, tartaric acid (2.2 g/m$^2$), lithium hydroxide (6.5 g/m$^2$), and cupric sulfate (2.7 g/m$^2$). A spreading layer of formulation 2, 3, or 5 (found in Table I below) was then coated over each reagent layer.

The elements were then evaluated by monitoring the change in the reflection optical density, $D_R$, occurring in these elements at 37° C. subsequent to spotting the spreading layer of each element with an aqueous liquid containing a known level of total protein. This was accomplished by reflection spectrophotometry by measuring the optical density of a beam of light passing through a 540 nm. interference filter and then the transparent film support, the reagent layer, and reflected back through these layers by the developed color spot formed in the element as a result of the interaction of the biuret reagent and the protein contained in the aqueous liquid spotted onto the element.

The spreading layer of the control element for the determination of total protein exhibited poor color spot quality as demonstrated by a "doughnuting" or "targeting" effect (as described earlier herein in the "Description of Related Art") appearing at low protein concentrations (3–7%). At higher concentrations (~10%), the "doughnuting" effect was not observed, indicating that the error varies with protein concentration. As previously stated, this "doughnuting" of spot color is believed to be caused by the migration of the protein to the circumference of the spot. The chemical reaction of serum protein in each of the multilayer elements using the biuret reagent described in this Example occurs at pH 13, which is above the isoelectric point (pI) of serum protein so that under these conditions protein exhibits a negative charge. Accordingly, as demonstrated by the elements of this Example (which elements contained spreading layer formulations 2, 3 and 5 of Table I), it was found that the introduction of an immobile polymeric material having positive charge-bearing functional groups into these spreading layer formulations substantially reduced and almost completely prevented the wandering of the negatively-charged proteins. Thus, the spot quality, as evaluated by reflection optical density measurements, of the elements showed little or no "doughnuting" effect, even at low protein concentration levels.

EXAMPLE 2

Incorporation of Negatively Charged Polymers into Spreading Layers of Analytical Elements for the Determination of Albumin Multilayer elements for the determination of albumin, employing a bromcresol green-dye binding method, exhibit a color spot quality problem, due to the migration of the albumin to the circumference of the spot, similar to that described in Example 1.

Because the reagent layer chemistry of the multilayer albumin elements employed in this Example were operational at pH 3.5–4.0, which is below the pI of albumin, it was determined in accord with the present invention that retention of albumin would be achieved by incorporating an immobilized polymeric material bearing negatively-charged functional groups into an otherwise conventional spreading layer formulation. Accordingly, a series of multilayer serum albumin elements was prepared as follows:

Transparent polyethylene terephthalate film supports were hand-coated from an aqueous coating dope with identical reagent layers having a dry coating composition composed of bromcresol green (0.03 g/m$^2$) as indicator dye, agarose (3.2 g/m$^2$) as binder, and succinic acid (0.5 g/m$^2$) as buffer. Then a spreading layer of formulation 3, 4 or 5 of Table I was coated over each reagent layer. The response of these elements to serum samples containing known levels of albumin (using samples having 3%, 5%, and 10% albumin concentrations) was evaluated by reflection spectrophotometry in a manner similar to that described in Example 1. However, in this Example the interference filter employed was a 600 nm. filter. As a result, it was found that the element of the invention, i.e., the element containing spreading layer formulation 4, exhibited substantially improved uniformity in spot density and reduction of the so-called "doughnut" effect in comparison to the control elements containing spreading layer formulations 3 or 5. Formulations 3 and 5 are controls because they contained polymers whose functional groups exhibited essentially neutral charge (i.e., diethylaminoalkyl cellulose) or positive charge (i.e., poly(vinylbenzyltrimethylammonium chloride) under these pH conditions. In contrast, spreading layer formulation 4 contained carboxymethyl cellulose having negative charge-bearing groups under the pH conditions (i.e., 3.5–4.0) existing in the elements of this Example.

EXAMPLE 3

Incorporation of Negatively Charged Polymers into the Spreading Layer of Analytical Elements for the Determination of Triglycerides Serum lipids are bound to and associated with large protein complexes (500,000 M.W.) and therefore diffuse very slowly laterally through conventional spreading layers of multilayer analytical elements of the type described in U.S. Pat. No. 3,992,158. Uniform spot densities can only be achieved in these analytical elements if the large lipoprotein complexes are initially spread uniformly across the spreading layer and the underlying triglyceride reagent layer contained in these elements. This was achieved in accord with the present invention, by incorporating charged polymers into the spreading layers of multilayer analytical elements for the analysis of triglyceride.

In this Example a series of multilayer analytical elements was prepared as follows: Transparent polyethylene terephthalate film supports were coated from an aqueous coating dope to form thereon triglyceride reagent layers containing an enzymatic composition interactive with triglyceride and a hydrogen peroxide-reactive indicator composition as described in *Research Disclosure*, Item 16146, p. 94–98, September, 1977, published by Industrial Opportunities, Ltd.,; Havant, Hampshire, England. Then a spreading layer of formulation 1 (control), 2 (control) or 4 of Table I was coated as described in U.S. Pat. No. 3,992,158 to form a blush polymer-reflecting spreading layer. It has been found that serum lipoprotein complexes, when spotted onto these multilayer analytical elements under pH conditions of about 7, tend to exhibit a net positive charge.

The elements were then evaluated as described in the above-referenced *Research Disclosure* publication using reflection spectrophotometry to evaluate the reflection optical density, $D_R$, formed in the element at 37° C. and 540 nm. as a function of time subsequent to spotting the spreading layer of each element with a liquid serum sample containing a known concentration of triglycerides. Both control spreading layer formulations, i.e., formulations 1 and 2, exhibited spot densities exhibiting pronounced "doughnuting" effects. The element in accord with the present invention having spreading layer formulation 4 containing carboxymethyl cellulose, a polymeric material which exhibited negatively charged groups under the pH conditions occurring in the reagent system of these elements, i.e., a pH of about 7, gave much improved spot density uniformity. In addition, color development in this element occurred much faster than in the control elements.

EXAMPLE 4

Incorporation of Negatively Charged Polymers into Homogeneous Spreading Layers of an Analytical Element for the Determination of Albumin To demonstrate the use of a polymeric material containing negative charge-bearing functional groups in a spreading layer formulation without the presence of reflecting vehicles such as $TiO_2$ or microcrystalline cellulose particles, multilayer analytical elements for the quantification of albumin were prepared as follows:

A transparent film support was hand coated from an aqueous coating dope to form an albumin reagent layer having the following dry composition: agarose (4.8 g/m$^2$) as binder, bromcresol green (0.3 g/m$^2$) indicating dye, (p-nonylphenoxy)glycerol (2.15 g/m$^2$) as surfactant, and succinic acid disodium salt (1.6 g/m$^2$) as buffer so that the albumin reagent system is employed at a pH of 3.7; and a spreading layer having formulation 6 described in Table I.

The spreading layer of this element gave improved spot uniformity relative to a control multilayer element which was identical, except that it contained a spreading layer having formulation 2 of Table I.

TABLE I

| Number | Spreading Layer | g/m$^2$ | Solvent (for coating of Spreading Layer) |
|---|---|---|---|
| 1. | TiO$_2$ | 45.0 | Acetone-dichloroethane-xylene |
|  | Cellulose Acetate | 6.6 | (2.7:1.0:1.7 parts by volume) |
|  | Octyl phenoxy polyethoxy ethanol (non-ionic) surfactant) | 1.4 |  |
| 2. | Avicel®$^1$ | 54.0 | H$_2$O-Isopropanol |
|  | Poly(vinylpyrrolidone) |  | (1:6 parts by volume) |
| 3. | Diethylaminoethyl Cellulose$^2$ | 10.0 | Isopropanol |
|  | Avicel®$^1$ | 32.0 |  |
| 4. | Carboxymethyl Cellulose$^3$ | 10.0 | Isopropanol |
|  | Avicel®$^1$ | 32.0 |  |
| 5. | Poly(vinylbenzyltrimethyl-ammonium chloride) | 5.4 | H$_2$O-Isopropanol |
|  |  |  | (1:6 parts by volume) |
|  | Avice®$^1$ | 86.0 |  |
|  | Poly(vinylpyrrolidone) | 2.2 |  |
| 6. | Carboxymethyl Cellulose | 86.0 | H$_2$O-Isopropanol |
|  | Poly(vinylpyrrolidone) | 4.3 | (1:7.5 parts by volume) |

$^1$Avicel is a trademark for microcrystalline cellulose particles sold by FMC Corp.
$^2$Diethylaminoethyl cellulose was ball milled in H$_2$O.
$^3$Carboxymethyl cellulose was ball milled in isopropanol.

The invention has been described in detail with particular reference to certain preferred embodiments thereof, but it will be understood that variations and modifications can be effected within the spirit and scope of the invention.

We claim:

1. In a multi-zone analytical element for the detection of a proteinaceous or protein-bound analyte in an aqueous liquid, said element comprising (1) a spreading zone to receive and distribute therewithin an applied sample of said aqueous liquid, and (2) a reagent zone in fluid contact with said spreading zone under conditions of use of said element, said reagent zone containing a composition interactive with said proteinaceous or protein-bound analyte to form a detectable species within said element, the improvement wherein said spreading zone comprises an immobile polymeric material which (a) is substantially non-interfering with respect to said interactive composition and (b) contains charge-bearing functional groups, said groups under conditions of use of said element exhibiting an electric charge opposite to that of said proteinaceous analyte or the protein portion of said protein-bound analyte.

2. A multi-zone analytical element as defined in claim 1 wherein said polymeric material has a molecular weight in excess of about 10,000.

3. A multi-zone analytical element as defined in claim 1 wherein said polymeric material is an anionic polymer.

4. A multi-zone analytical element as defined in claim 1 wherein said polymeric material contains a charge-bearing functional group selected from the group consisting of carboxy, sulfonic, sulfonate, and phosphonic groups.

5. A multi-zone analytical element as defined in claim 1 wherein said polymeric material is carboxymethyl cellulose.

6. A multi-zone analytical element as defined in claim 1 wherein said polymeric material contains a charge-bearing functional group which exhibits a positive charge at a pH of at least about 8.0.

7. A multi-zone analytical element as defined in claim 1 wherein said polymeric material contains an amino group.

8. A multi-zone analytical element as defined in claim 1 wherein said polymeric material is a cationic polymer.

9. A multi-zone analytical element as defined in claim 1 wherein said polymeric material is a cationic polymer containing an ammonium or a phosphonium group.

10. A multi-zone analytical element as defined in claim 1 wherein said polymeric material is poly(vinyl benzyltrimethyl ammonium chloride).

11. An integral multilayer analytical element for the detection of a proteinaceous or protein-bound analyte in an aqueous fluid, said element comprising a radiation-transmissive support bearing a reagent layer and, superposed thereover, an isotropically porous spreading layer, (a) said reagent layer being in fluid contact with said spreading layer under conditions of use of said element and comprising a composition interactive with said analyte to provide a radiometrically detectable change within said element, and (b) said spreading layer comprising an immobile polymeric material which (a) is substantially non-interfering with respect to said interactive composition and (b) contains charge-bearing functional groups, said groups under conditions of use of said element exhibiting an electric charge opposite to that of said proteinaceous analyte or the protein portion of said protein-bound analyte.

12. A method for the analysis of a proteinaceous or protein-bound analyte in an aqueous liquid sample, said method comprising
   (1) contacting said aqueous liquid sample together with a multi-zone analytical element having
      (a) a spreading zone to receive and distribute therewithin said sample and
      (b) a reagent zone in fluid contact with said spreading zone under conditions of use of said element, said reagent zone containing a composition interactive with said proteinaceous or protein-bound analyte to provide a detectable change in said element, said spreading zone containing an immobile polymeric material which (i) is substantially non-interfering with respect to said interactive composition and (ii) contains charge-bearing functional groups, said groups under conditions of use of said element exhibiting an electric charge opposite to that of said proteinaceous analyte or the protein portion of said protein-bound analyte; and
   (2) detecting, after a predetermined time, the detectable change produced in said element.

13. An integral multilayer analytical element as defined in claim 11 wherein said element is for the detection of total protein, said element comprising in the reagent layer thereof a composition interactive with total protein to provide said detectable change, and said element comprising as said polymeric material contained in the spreading layer thereof a cationic polymer or a polymer having amino groups appended thereto.

14. An integral multilayer analytical element as defined in claim 11 wherein said element is for the detection of albumin, said element comprising in the reagent layer thereof a composition interactive with albumin to provide said detectable change, and said element comprising an anionic polymer as said polymeric material contained in the spreading layer thereof.

15. An integral multilayer analytical element as defined in claim 11 wherein said element is for the detection of triglyceride, said element comprising in the reagent layer thereof a composition interactive with triglyceride to provide said detectable change, and said element comprising an anionic polymer as said polymeric material contained in the spreading layer thereof.

* * * * *